United States Patent
Kremer et al.

(10) Patent No.: US 9,877,687 B2
(45) Date of Patent: Jan. 30, 2018

(54) COLLIMATION FOR DISTANCED FOCAL SPOTS

(71) Applicant: KONINKLIJKE PHILIPS N.V., Eindhoven (NL)

(72) Inventors: Frans Henk Kremer, Eindhoven (NL); Robert Derk Jan Hendrik Hofsink, Son (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 14/888,757

(22) PCT Filed: May 6, 2014

(86) PCT No.: PCT/EP2014/059164
§ 371 (c)(1),
(2) Date: Nov. 3, 2015

(87) PCT Pub. No.: WO2014/180809
PCT Pub. Date: Nov. 13, 2014

(65) Prior Publication Data
US 2016/0081636 A1    Mar. 24, 2016

(30) Foreign Application Priority Data
May 8, 2013  (EP) .................................... 13166998

(51) Int. Cl.
*G21K 1/02*  (2006.01)
*A61B 6/06*  (2006.01)
(Continued)

(52) U.S. Cl.
CPC .............. *A61B 6/06* (2013.01); *A61B 6/4007* (2013.01); *A61B 6/4021* (2013.01);
(Continued)

(58) Field of Classification Search
CPC ........... A61B 6/00; A61B 6/06; A61B 6/4028; A61B 6/4007; A61B 6/4021; G21K 1/00; G21K 1/02; G21K 1/025; G21K 1/04
(Continued)

(56) References Cited

U.S. PATENT DOCUMENTS 1,163,987 A   12/1915 Eggers
6,256,369 B1 * 7/2001 Lai .......................... A61B 6/032
378/14

(Continued)

FOREIGN PATENT DOCUMENTS

DE    8127102 U1    3/1985
DE    9103670 U1    5/1991
(Continued)

*Primary Examiner* — Jurie Yun

(57) ABSTRACT

The present invention relates to collimation of X-ray radiation and comprises an X-ray source arrangement for medical imaging, the X-ray source arrangement comprising an X-ray source, and an X-ray beam shutter device. The X-ray source has at least at a first and a second focal spot position distanced apart from each other in a direction transverse to a main radiation direction. The X-ray beam shutter device comprises at least a first pair of shutters defining a first diaphragm, and at least a second pair of shutters defining a second diaphragm. The first pair of shutters is configured for alignment with a first line-of-sight between the first focal spot position and a center of a detector, and the second pair of shutters is configured for alignment with a second line-of-sight between the second focal spot position and a center of a detector. The first and the second diaphragm partly overlap.

9 Claims, 5 Drawing Sheets

(51) Int. Cl.
*A61B 6/00* (2006.01)
*G21K 1/04* (2006.01)
*A61B 6/02* (2006.01)

(52) U.S. Cl.
CPC .......... *A61B 6/4028* (2013.01); *A61B 6/4035* (2013.01); *G21K 1/04* (2013.01); *A61B 6/022* (2013.01); *A61B 6/482* (2013.01)

(58) Field of Classification Search
USPC .......... 378/62, 147, 148, 149, 150, 152, 153
See application file for complete search history.

(56) References Cited

U.S. PATENT DOCUMENTS

| | | | |
|---|---|---|---|
| 7,844,032 B2 * | 11/2010 | Vermilyea | G21K 1/025 378/149 |
| 2008/0237472 A1 | 10/2008 | Uribe et al. | |
| 2010/0308229 A1 | 12/2010 | Bertram et al. | |
| 2011/0188624 A1 | 8/2011 | Ren et al. | |
| 2012/0063565 A1 | 3/2012 | Klingenbeck | |

FOREIGN PATENT DOCUMENTS

| | | |
|---|---|---|
| EP | 0142841 A2 | 5/1985 |
| EP | 1120086 A1 | 8/2001 |
| EP | 1677254 A1 | 7/2006 |
| FR | 790078 A | 11/1935 |
| GB | 2035769 A | 6/1980 |
| JP | 2004089445 A | 3/2004 |
| WO | 2012058731 A1 | 5/2012 |

* cited by examiner

COLLIMATION FOR DISTANCED FOCAL SPOTS

CROSS-REFERENCE TO PRIOR APPLICATIONS

This application is the U.S. National Phase application under 35 U.S.C. §371 of International Application No. PCT/EP2014/059164, filed on May 6, 2014, which claims the benefit of European Patent Application No. 13166998.8, filed on May 8, 2013. These applications are hereby incorporated by reference herein.

FIELD OF THE INVENTION

The present invention relates to collimation of X-ray radiation, and relates in particular to an X-ray source arrangement for medical imaging and to a medical X-ray imaging system incorporating such an arrangement.

BACKGROUND OF THE INVENTION

In medical X-ray imaging, the generated X-ray beam may be collimated, for example in order to fit to the size of the detector. A reason may be a requirement to ensure that all radiation, to which a patient may be exposed to, is emitted towards a detector to be detected with the respective attenuation provided by the object. Besides the actual size limitation of the radiated beam, also wedge elements may be provided as attenuation filters in the X-ray beam. For example, US 2010/0308229 A1 describes the provision of a wedge-shaped attenuation filter adjustably positioned in the cone beam to selectively attenuate the beam for improved image quality. However, it has been shown that in case of, for example, two focal spots displaced apart from each other, the field of view is limited due to cutting off a part of the respective other image, for example when having fixed shutters.

SUMMARY OF THE INVENTION

There may thus be a need for X-ray collimation suitable for focal spots spaced apart from each other with improved use of the provided radiation beam.

The object of the present invention is solved by the subject-matter of the independent claims, wherein further embodiments are incorporated in the dependent claims. It should be noted that the following described aspects of the invention apply to the X-ray source arrangement for medical imaging as well as the medical X-ray imaging system.

According to the present invention, an X-ray source arrangement for medical imaging is provided, comprising an X-ray source and an X-ray beam shutter device. The X-ray source is configured to generate X-ray radiation at least at a first and a second focal spot position distanced apart from each other in a direction transverse to a main radiation direction. The X-ray beam shutter device comprises at least a first pair of shutters defining a first diaphragm for a first X-ray beam generated at the first focal spot position, and at least a second pair of shutters defining a second diaphragm for a second X-ray beam generated at the second focal spot position. The first and the second diaphragm partly overlap.

The first and the second pair of shutters each comprise an outer shutter element for limiting the diaphragm on an outer side arranged opposite an overlapping portion of the diaphragm. The outer shutter elements comprise a solid/opaque structure in X-ray radiation direction. The first and the second pair of shutters further comprise a respective first and second inner shutter element for limiting the diaphragm on an inner side arranged at least partly in the overlapping portion. The first inner shutter element and the second inner shutter element each comprise a focused grid structure. The grid structure of the first inner shutter element comprises a plurality of first X-ray passages that are focused on the second focal spot position; and the grid structure of the second inner shutter element comprises a plurality of second X-ray passages that are focused on the first focal spot position.

Advantageously, the arrangement according to the invention provides a respective optimized collimation for the first or the second focal spot position. Thus, an optimized use of the generated X-ray beam is ensured.

Additionally, although a shutter element is arranged in the diaphragm, i.e. in the so-to-speak opening, the respective shutter element is acting as beam size limiting element for X-ray radiation originating from a single X-ray focal spot position only; radiation originating from the other X-ray focal spot position can pass the shutter element due to the alignment of the X-ray passages provided in the grid structure.

The passage of X-rays through the shutter elements is such that only a minimum amount of X-ray radiation is attenuated and absorbed by the grid structure, and the main portion of the X-ray radiation can pass the respective shutter element. The boundary portions of the X-ray passages, i.e. the so-to-speak sidewalls of the passages, provided by the grid structure are acting as absorbing structure, or X-ray non-transparent structure, from directions in an oblique angle to the direction of the X-ray passages, in particular for X-ray radiation from the respective other focal spot position. Thereby, a geometric selective grade of X-ray transmission is provided.

The term "pair of shutters" relates to, for example, a first and a second shutter. In another example, the term "pair" also relates to three, four, five, six, or more shutters defining the respective diaphragm. It is in particular noted that the respective shutters may be provided with different contours, for example as straight boundary lines or with curved boundary lines, or boundary lines comprising of several line segments.

The X-ray beam shutter device is also referred to as collimation device or collimation providing a diaphragm for X-ray radiation.

The direction, in which the focal spot positions are displaced, is provided transverse to a direction between a cathode and the anode.

In another example, the direction, in which the focal spot positions are displaced, is transverse to the projection direction of the X-ray radiation. For example, the direction is referred to as x-direction. In one example, in case of a rotating anode, the displacement direction is parallel to the direction, in which the anode is spinning, i.e. parallel to a tangential line to a circular spinning plane. The displacement direction may be provided transverse, for example orthogonal, to an axis of rotation.

The X-ray source may be a rotating anode comprising a target structure providing the at least two focal spot positions. In a further example, the X-ray source comprises two separate anodes or target structures for providing the at least two focal spot positions. In a further example, a plurality of X-ray sources, for example X-ray nano-tubes, is provided to form a respective cluster of a number of nano-tubes for the first focal spot position and the further number of nano-tubes for the second focal spot position.

The first and the second diaphragm at least partly overlap in the x-direction.

The two focal spot positions are provided, in one example, for stereo X-ray imaging. In another example, the two focal spot positions are provided for dual energy X-ray imaging.

The term "focused" relates to focusing, i.e. aligning in a radial manner, to the respective focal spot position. The correct focusing is the case in a predetermined distance, in one example.

In another example, the focal spot positions are adjustable or variable. In such case at least the inner shutter elements are adjustable or movable. For example, the elements are movable in a radial direction parallel to a main X-ray radiation direction. For example, the elements can alternatively or in addition be movable or adjustable in a radiation transverse to the main X-ray radiation direction. In another example, the inner shutter elements are movable in similar directions as provided by the movable focal spot positions.

In another example, the X-ray passages are provided by lamella-like elements that are adjustable in their focusing alignment to compensate for focal spot alterations.

In an example, an alignment mechanism of the shutter elements is provided.

According to an example, the first inner shutter element is arranged at least partly in an X-ray beam of the second focal spot position, the shutter element being X-ray transmissive for radiation from the second focal spot position. The second inner shutter element is arranged at least partly in an X-ray beam of the first focal spot position, the shutter element being X-ray transmissive for radiation from the first focal spot position.

The term "X-ray transmissive" refers to the grid structure with its passage ways for X-ray radiation in the receiving direction. "X-ray transmissive" refers to a grade of X-ray transmission in a non-attenuated manner by at least approximately 50 percent, for example 70 percent, for example 90 percent, for example 95%, or more percent.

According to an example, the first inner shutter element is movable on a first circular track around the second focal spot position, and the second inner shutter element is movable on a second circular track around the first focal spot position.

In an example, a control unit is provided to control the movement of the shutter elements by an actuator arrangement.

According to an example, the inner and outer shutter elements are provided with ring-segment cross-sections with a center at one of the focal spot positions, wherein (i) the first outer shutter element and the second inner shutter element are provided concentric to the first focal spot position, and (ii) the first inner shutter element and the second outer shutter element are provided concentric to the second focal spot position.

According to an example, the first and second focal spot positions are provided as two static positions alternatively switched per frame for X-ray imaging, and the first and second inner shutter elements remain temporarily fixed during the X-ray imaging.

According to a further aspect of the invention, a medical X-ray imaging system is provided, comprising, as an X-ray generating device, an X-ray source arrangement according to one of the above-mentioned examples, an X-ray detector, and an object-receiving device. The object-receiving device is positionable between the X-ray generating device and the X-ray detecting device.

The X-ray detecting device may be a detector provided such that the radiation from the first focal spot and the radiation from the second focal spot are detectable after radiating an object of interest, for example a patient. In an example, the radiation from the first focal spot is detected on the detector area as the radiation from the second focal spot. In an example, the focal spot is moved in relation to the object-receiving device.

Advantageously, within the source arrangement, the first pair of shutters is configured for alignment with a first line-of-sight between the first focal spot position and a center of a detector. The second pair of shutters is configured for alignment with a second line-of-sight between the second focal spot position and a center of a detector. Within the context of this invention, "alignment" of a pair of shutters with a line-of-sight is understood to mean that a center or central portion of an aperture in a diaphragm defined by the shutters is to be aligned with the line-of-sight. In case of non-static focal spots, this implies that shutters may need to be repositioned in operation, in order for such alignment to be maintained.

The alignment is provided in at least one alignment direction. In a further example, two alignment directions are provided in a transverse manner.

According to an example, the first and second pair of shutters comprise a respective first and second outer shutter element for limiting the diaphragm on an outer side arranged opposites an overlapping portion of the diaphragm, and the first and the second pair of shutters comprise a respective first and second inner shutter element for limiting the diaphragm on an inner side arranged at least partly in the overlapping portion. The outer shutter elements are adjustably fixed for X-ray imaging. The inner shutter elements are movable and configured for temporal alignment with the first line-of-sight between the first focal spot position and the center of the detector, and for temporal alignment with the second line-of-sight between the second focal spot position and the center of the detector. The first and the second focal spot positions are useable for X-ray radiation in an alternate manner during X-ray imaging. The first and second inner shutter elements are alternately alignable during the X-ray imaging, wherein the respective other second or first inner shutter element is movable out of the X-ray radiation. A control unit is provided to control the alignment of the first and second inner shutter elements by an actuator arrangement.

Thus, according to the invention, an X-ray beam may be provided from two different focal spot positions, and a beam limiting arrangement is providing an opening, also called aperture, for the first focal spot position and an opening/aperture for the second focal spot position. The two apertures/openings overlap. Nevertheless, the provided shutter elements ensure that a beam size limitation, i.e. X-ray beam collimation, is properly aligned for the respective first and second focal spot position. For example, shutter elements may be provided with static positions, for example by providing an X-ray transparent structure aligned for the respective other focal spot position and being X-ray opaque for the respective focal spot position. In a further example, the shutter elements are moving dynamically in order for the diaphragm apertures to align with the respective X-ray focal spots.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
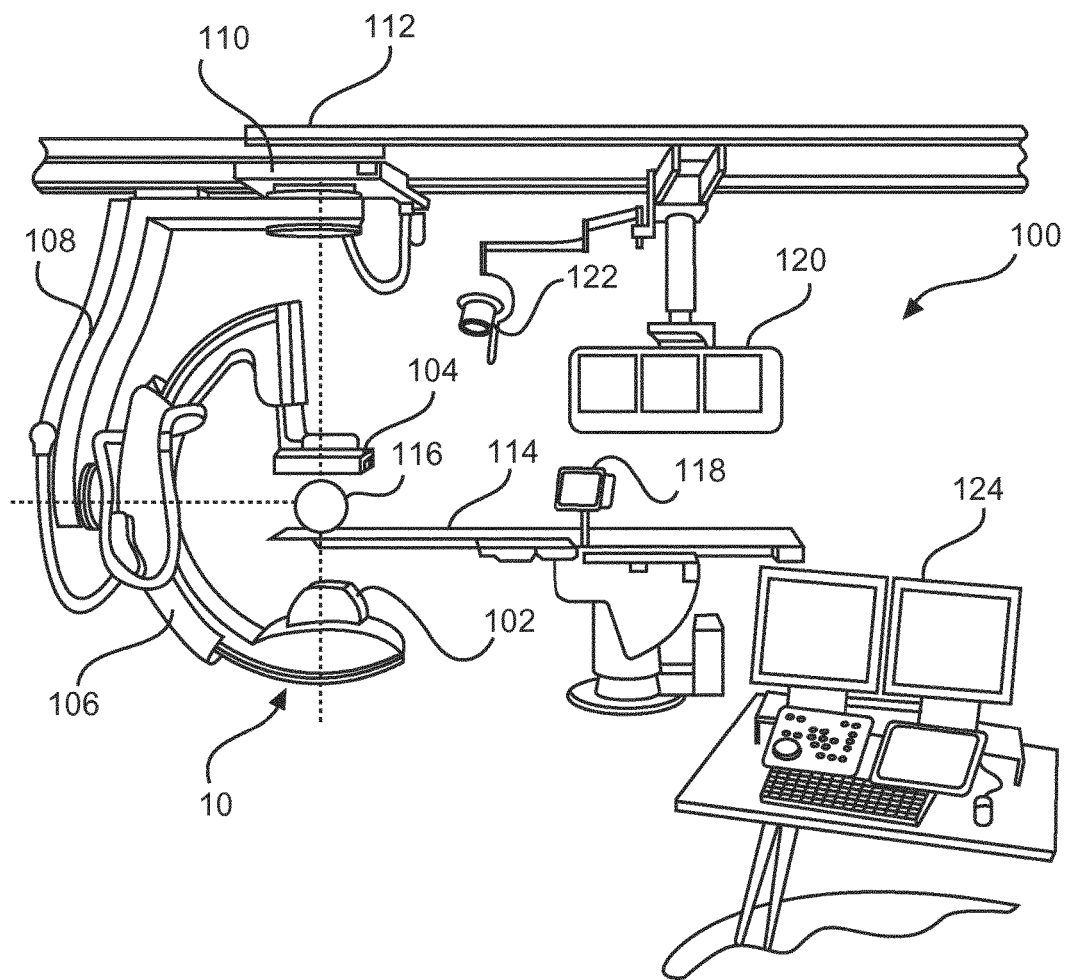
FIG. 1 shows an example of a medical X-ray imaging in a schematic perspective setup.

FIG. 1 shows a medical X-ray imaging system 100 with an X-ray generating device 102, and an X-ray detecting device 104. As an example, the X-ray generating device 102, i.e. an X-ray source, and the X-ray detecting device 104, i.e. an X-ray detector, are arranged on opposing ends of a C-arm structure 106, movably mounted by a ceiling suspension 108 to a movable ceiling support device 110 attached to a ceiling 112. Further, an object-receiving device 114 is provided, wherein the object-receiving device 114 is arranged between the X-ray generating device 102 and the X-ray detecting device 104. For example, the object-receiving device 114 is a patient table for receiving a patient. An object 116 is indicated by a circular structure.

Further, in the vicinity of the above-described arrangement, further equipment is indicated, for example a control interface 118 for controlling the X-ray imaging system 100, or a display arrangement 120, as well as a lighting arrangement 122. Further, a control station 124 is indicated in the foreground.

It is explicitly noted that although a stationary C-arm system is shown in FIG. 1, according to the present invention also other medical X-ray imaging systems are provided, although not further shown in detail, such as, for example, movable C-arm systems, or CT systems with a gantry and a rotating X-ray source/X-ray detector configuration. Further, also fixed X-ray imaging systems may be provided, as well as partly fixed X-ray imaging systems, such as systems where only the detector can be adjusted and the X-ray source is static. Further, also different types of medical X-ray imaging systems with respect to the patient arrangement are provided, for example, as shown, arrangements with a patient lying during the imaging, or where the patient is in a standing-up position, for example for lung/chest imaging, or also for mammography X-ray imaging, and others.

Generally, the X-ray generating device is provided as an X-ray source arrangement 10 according to one of the below described examples.

Figure 2:
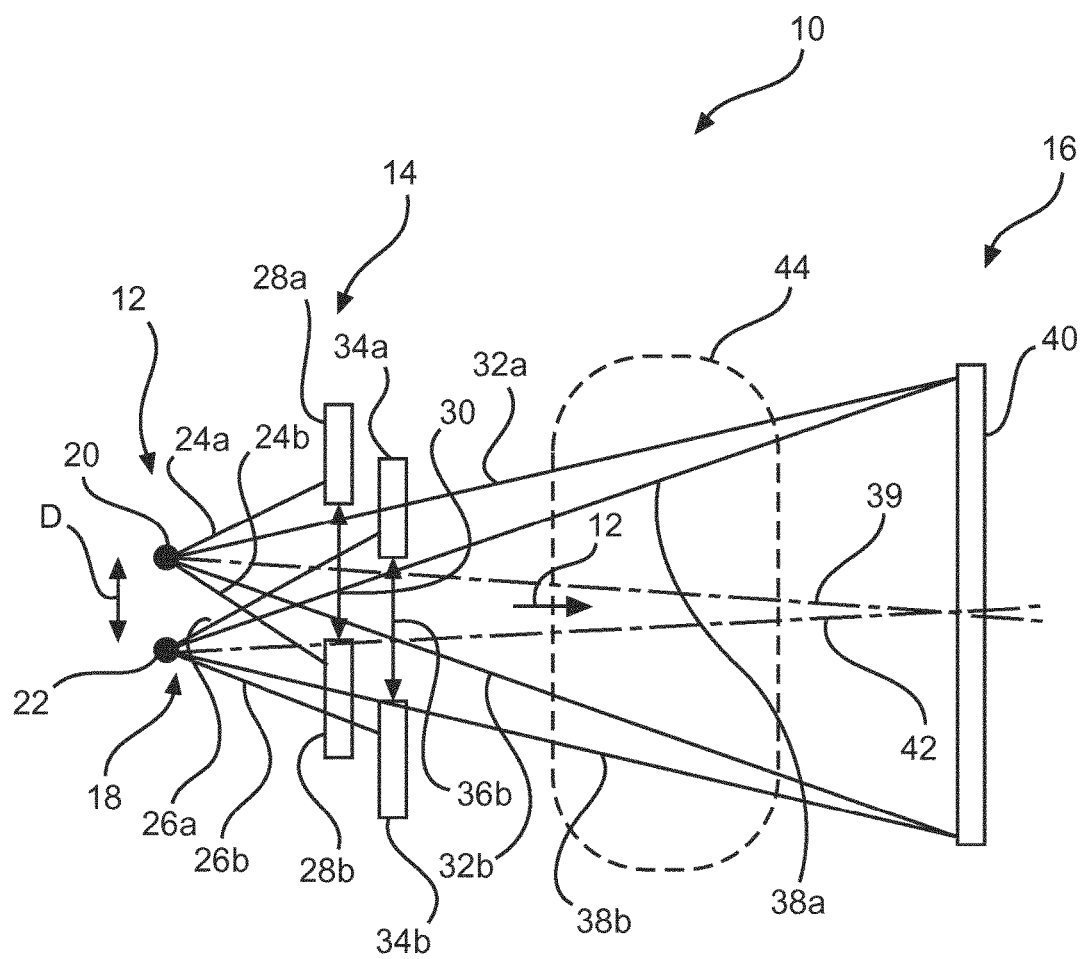
FIG. 2 shows an example of an X-ray source arrangement in a schematic cross-section.

FIG. 2 shows an example of an X-ray source arrangement 10 for medical imaging in a schematic cross-section. The X-ray source arrangement 10 comprises an X-ray source 12, and an X-ray beam shutter device 14. Further, a detector device 16 is shown, although not necessarily being a component of the X-ray source arrangement.

The X-ray source 12 is configured to generate X-ray radiation 18 at least at a first focal spot position 20 and at a second focal spot position 22. The first and the second focal spot position 20, 22 are distanced apart from each other in a direction D transverse to an main radiation direction R. The direction D is indicated with a double arrow and the main radiation direction R is indicated with a single arrow. A pair of first outer lines 24a, 24b indicates X-ray radiation generated at the first focal spot position 20. A second pair of outer lines 26a, 26b is indicating X-ray radiation generated at the second focal spot position 22.

The X-ray beam shutter device 14 comprises at least a first pair of shutters 28, indicated with reference characters 28a and 28b, defining a first diaphragm 30, indicated by a double arrow, for a first X-ray beam generated at the first focal spot position. A first pair of beam boundary lines 32a and 32b is indicating the X-ray beam passing the first diaphragm 30.

Further, at least a second pair of shutters 34 is provided, indicated with reference characters 34a and 34b, defining a second diaphragm 36 for a second X-ray beam generated at the second focal spot position 22. A second pair of beam boundary lines 38a and 38b is indicating the respective X-ray beam passing the second aperture 36.

The first pair of shutters 28 is configured for alignment with a first line-of-sight 39 between the first focal spot position 20 and a center of a detector, for example the detector panel 40. The second pair of shutters 34 is configured for alignment with a second line-of-sight 42 between the second focal spot position 22 and a center of a detector.

As can be seen, the first and the second diaphragm 30, 36 partly overlap with respect to X-ray radiation direction R.

A dotted line structure 44 indicates an object arranged between the X-ray source 12 and the X-ray detector 16 for medical imaging. The object may be a patient, for example.

Figure 3:
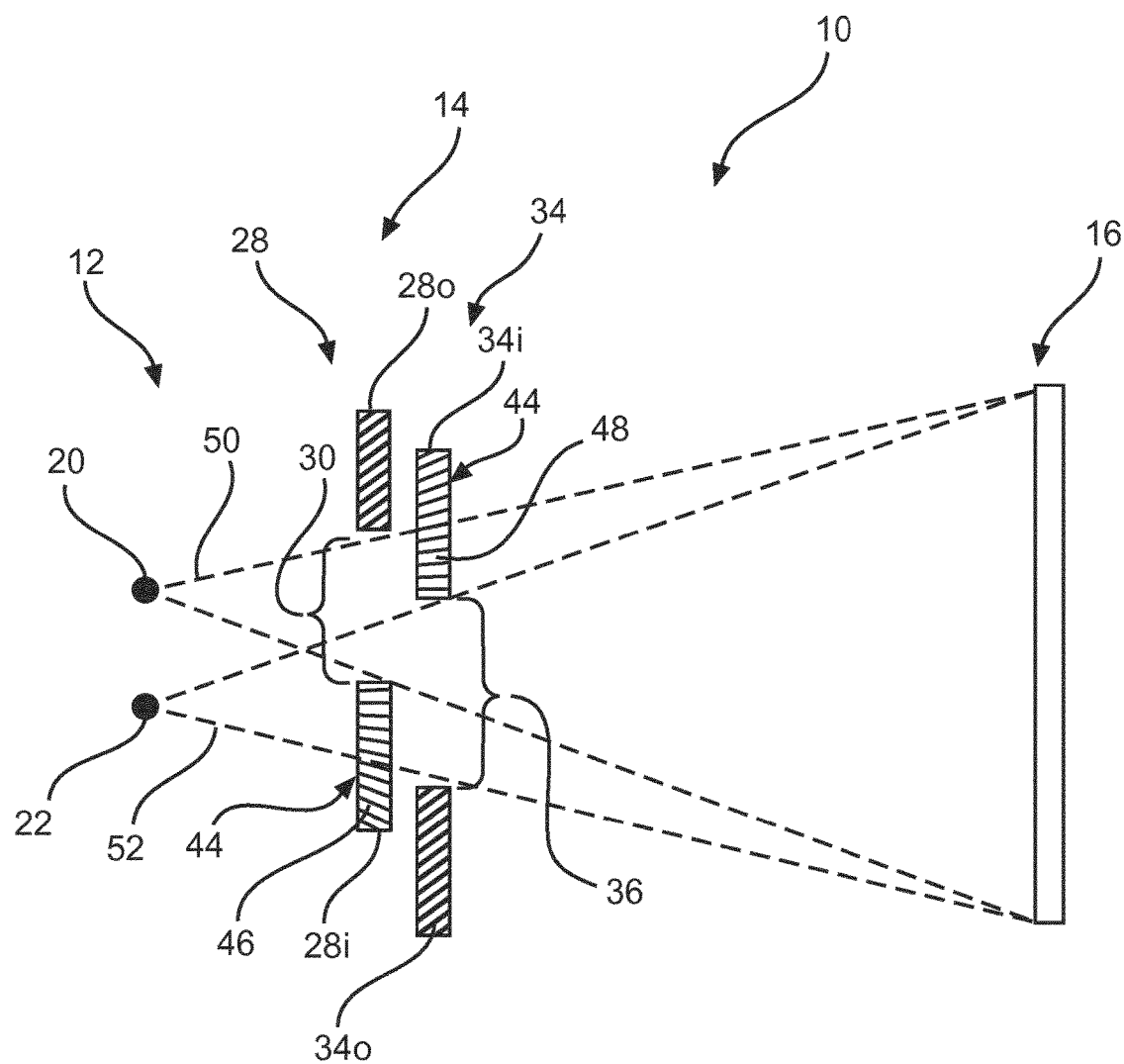
FIG. 3 shows a further aspect of the X-ray source arrangement.

FIG. 3 shows a further aspect of the X-ray source arrangement 10, in particular the focal grids. In the Figure, static focal spots are shown; however, the focal spots may also be provided as movable focal spots (as discussed further below).

The first and the second pair of shutters 28, 34, each comprise an outer shutter element for limiting the diaphragm on an outer side arranged opposite an overlapping portion of the diaphragm. The outer shutter elements are indicated with index "$_O$", i.e. with reference character $28_O$ and $34_O$ for the first outer shutter element and the second outer shutter element, respectively. The outer shutter elements $28_O$, $34_O$ comprise a solid structure in X-ray radiation direction.

It is noted that FIG. 2 shows the first pair of shutters 28 with reference characters 28a and 28b, and the second pair of shutters 34 with reference characters 34a and 34b. In an example, the shutter element 28a is referred to as the first outer shutter element, such as the first outer shutter element $28_O$, and the shutter element 28b is referred to as the first inner shutter element $28_I$; and the shutter element 34a is referred to as the second outer shutter element, such as the second outer shutter element $34_O$, and the shutter element 34b is referred to as the second inner shutter element $34_I$.

The order of the first and the second shutter with respect to the radiation direction is also provided in a reversed manner in an example.

The first and the second pair of shutters 28, 34 comprise a respective first and second inner shutter element for limiting the diaphragm on an inner side arranged at least partly in the overlapping portion. The inner shutter element is indicated with index "$_I$", i.e. the first inner shutter element is indicated with reference character $28_I$, and the second inner shutter element with reference character $34_I$. The first inner shutter element $28_I$ and the second inner shutter element $34_I$ each comprise a focused grid structure 44. The grid structure of the first inner shutter element $28_I$ comprises a plurality of first X-ray passages 46 that are focused on the second focal spot position 22. The grid structure of the second inner shutter element $34_I$ comprises a plurality of second X-ray passages 48 that are focused on the first focal spot position 20.

In FIG. 3, a first pair of dotted lines 50 indicates a first X-ray beam, and a second pair of dotted lines 52 indicates a second X-ray beam. The first X-ray beam is passing the first diaphragm 30, and the second X-ray beam is passing the second diaphragm 36. It is noted that the complete X-ray radiation (beam) generated from the respective first and second focal spot positions 20, 22, as indicated in FIG. 2, is not further shown for the sake of simplicity in FIG. 3.

As indicated above, the first inner shutter element $28_I$ is arranged at least partly in the X-ray beam 52 from the second focal spot position 22. The first inner shutter element $28_I$ is X-ray transmissive for radiation from the second focal spot position 22 and is in the same time X-ray blocking for radiation from the first focal spot position 20 in order to provide the beam limiting or beam size collimating effect.

The second inner shutter element $34_I$ is arranged at least partly in the X-ray beam 50 of the first focal spot position 20. The second inner shutter element $34_I$ is X-ray transmissive for radiation from the first focal spot position 20, and X-ray opaque or X-ray beam limiting for X-ray radiation from the second focal spot position 22 in order to provide the mentioned collimating function.

It must be noted that in FIG. 3, the first pair of shutters 28 is provided in a first plane, and the second pair of shutters 34 is provided in a second plane. However, in a further example, the outer shutter elements, i.e. the first outer shutter element $28_O$ and the second outer shutter element $34_O$ are provided in a common outer shutter element plane. The inner shutter elements, i.e. the first inner shutter element $28_I$ and the second inner shutter element $34_I$, are provided in a common inner shutter elements plane (not further shown in detail).

Figure 4:
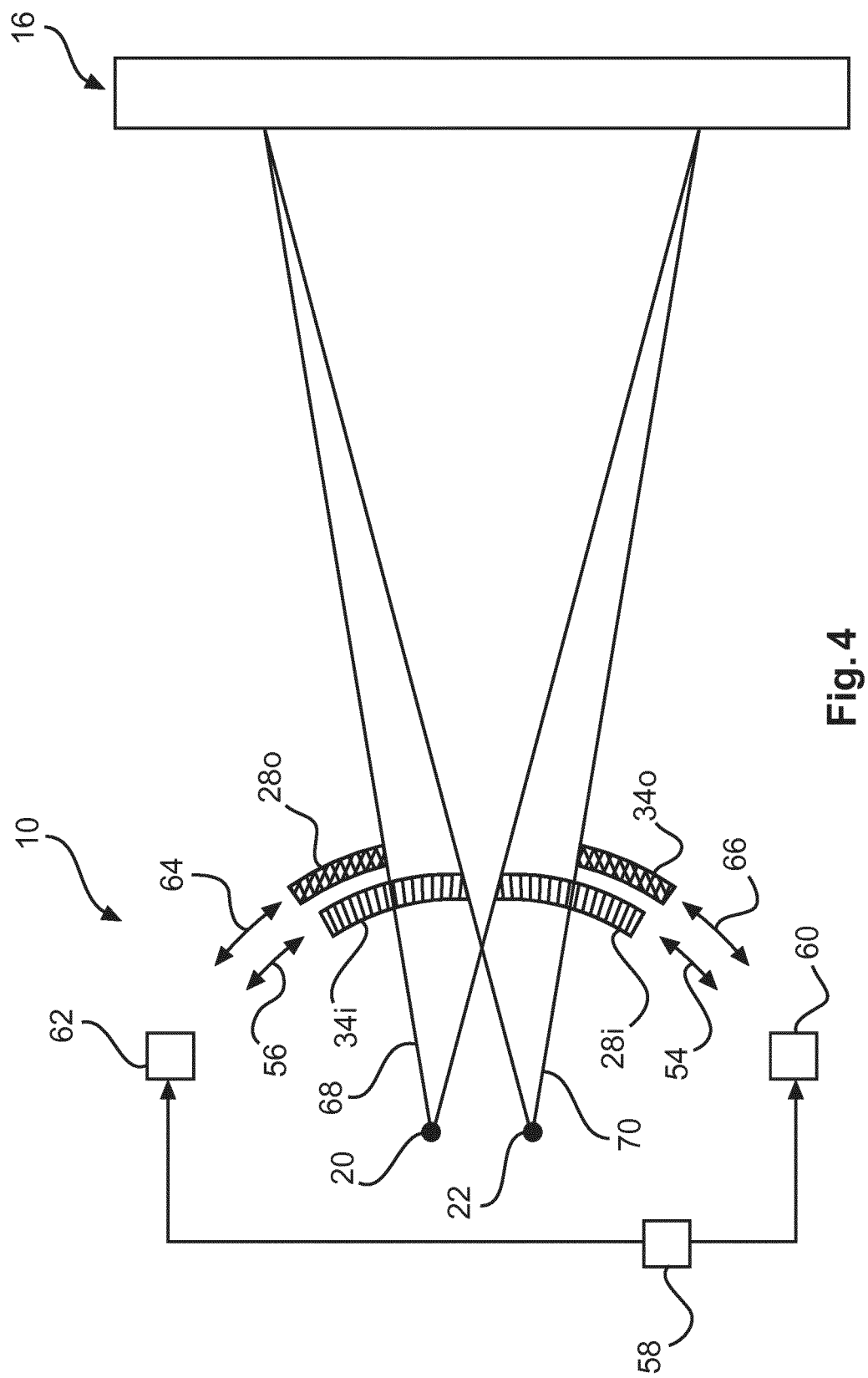
FIG. 4 shows an alternative embodiment of the X-ray source arrangement.

FIG. 4 shows a further embodiment of the X-ray source arrangement 10. The first inner shutter element $28_I$ is movable on a first circular track, indicated with a first double arrow 54 around the second focal spot position 22. The second inner shutter element $34_I$ is movable on a second circular track, indicated with a second double arrow 56 around the first focal spot position 20.

For example, a control unit 58 may be provided to control the movement of the shutter elements by a respective first and second actuator arrangement 60, 62.

According to a further example, also shown in combination with the above-mentioned example, also the first outer shutter element $28_O$ is movable on a first outer circular track, indicated with a first outer double arrow 64. Also the second outer shutter element $34_O$ is movable on a second outer circular track, indicated with a second outer double arrow 66. However, it must be noted that the movement of the outer shutter elements and the movement of the inner shutter elements are provided as separate options. Although the two options are shown in FIG. 4, it is explicitly noted that the two options are also provided independent from each other, i.e. this respective option can also be taken separately, i.e. without the other respective option, as additional function.

A first pair of lines indicates a first X-ray beam 68, generated at the first focal spot position 20, and a second pair of lines indicates a second X-ray beam 70, generated at the second focal spot position 22.

For example, the inner shutter elements $28_I$, $34_I$ are adjusted for an image acquisition procedure, whereas they remain fixed in their adjusted position during the X-ray image acquisition procedure.

In another example, the inner shutter elements $28_I$, $34_I$ are adjusted during the image acquisition procedure. For example, they are moved on the circular track 54, 56 such that the complete X-ray beam passes through the lamella structure of the respective inner shutter element.

In another example, the X-ray beam only partly passes through the lamella structure, as indicated in FIG. 4, and a different of attenuation thus provided is compensated by image processing in an image processor (not further shown).

It is further noted that FIG. 4 shows the shutter elements, i.e. the inner shutter elements and the outer shutter elements with a ring-segment cross-section, which will be further explained below.

However, it is further provided that the respective shutter elements are provided with a rectangular structure. In case of moving the shutter elements, in particular the inner shutter elements with the first and second X-ray passages 46, 48, the movement will be aligned to the respective focusing to the respective first and second focal spot position 20, 22. However, the lamella structure can be arranged in a shutter element with different cross-section. Of course, the outer shutter elements $28_O$, $34_O$ can also be provided with different cross-sections, and may also be moved along other tracks than a circular track.

According to a further example, also indicated in FIG. 4, the inner and outer shutter elements $28_I$, $34_I$ and $28_O$, $34_O$ are provided with ring-segment cross-sections with a center at one of the focal spot positions. The first outer shutter element $28_O$ and the second inner shutter element $34_I$ are provided concentric to the first focal spot position 20. The first inner shutter element $28_I$ and the second outer shutter element $34_O$ are provided concentric to the second focal spot position 22.

The circular shape of the focused grid provides the advantage that the amount of X-ray being absorbed by the structure is uniform to a large extent across the radiated beam, and thus across a major part of the part of the detector covered by the collimated X-ray beam, or also across the entire surface of the part of the detector covered by the collimated X-ray beam, in one example.

In another example, the focal spot is not entirely covered by an inner shutter, i.e. an inner shutter element with its X-ray passages is arranged only partly in the X-ray beam from the focal spot. Hence, a part of the detector may be radiated directly from the focal spot, without the inner shutter in between.

It must be noted that this respective concentric arrangement has been described above in combination with the movable on the circular tracks in FIG. 4. However, the arrangement of the ring-segment cross-sections may also be provided without the possibility to move the shutter elements on circular tracks.

In a further example, the inner shutter elements $28_I$, $34_I$ are provided with a ring-segment cross-section, and the outer shutter elements $28_O$, $34_O$ are provided with different cross-sections, for example linear cross-sections or rectangular cross-sections, or other forms.

According to an example, as indicated in FIG. 4, the first and second focal spot positions 20, 22 are provided as two static positions alternatively switched per frame for X-ray imaging. The first and second inner shutter elements $28_I$, $34_I$ remain temporarily fixed during the X-ray imaging.

In a further example, the first and second focal spot positions 20, 22 are provided as movable positions (not further indicated in FIG. 4). The first and second inner shutter elements $28_I$, $34_I$ are adjustable to compensate for altering of the focal spot positions. For example, in case the second focal spot position 22 in FIG. 4 would move upwards towards the first focal spot position 20, also the first inner shutter element $28_I$ would have to moved or adjusted in its position accordingly to match i.e. to align the grid structure of the X-ray passages with the moved second focal spot position 22. However, this is not further shown in FIG. 4.

Figure 5:
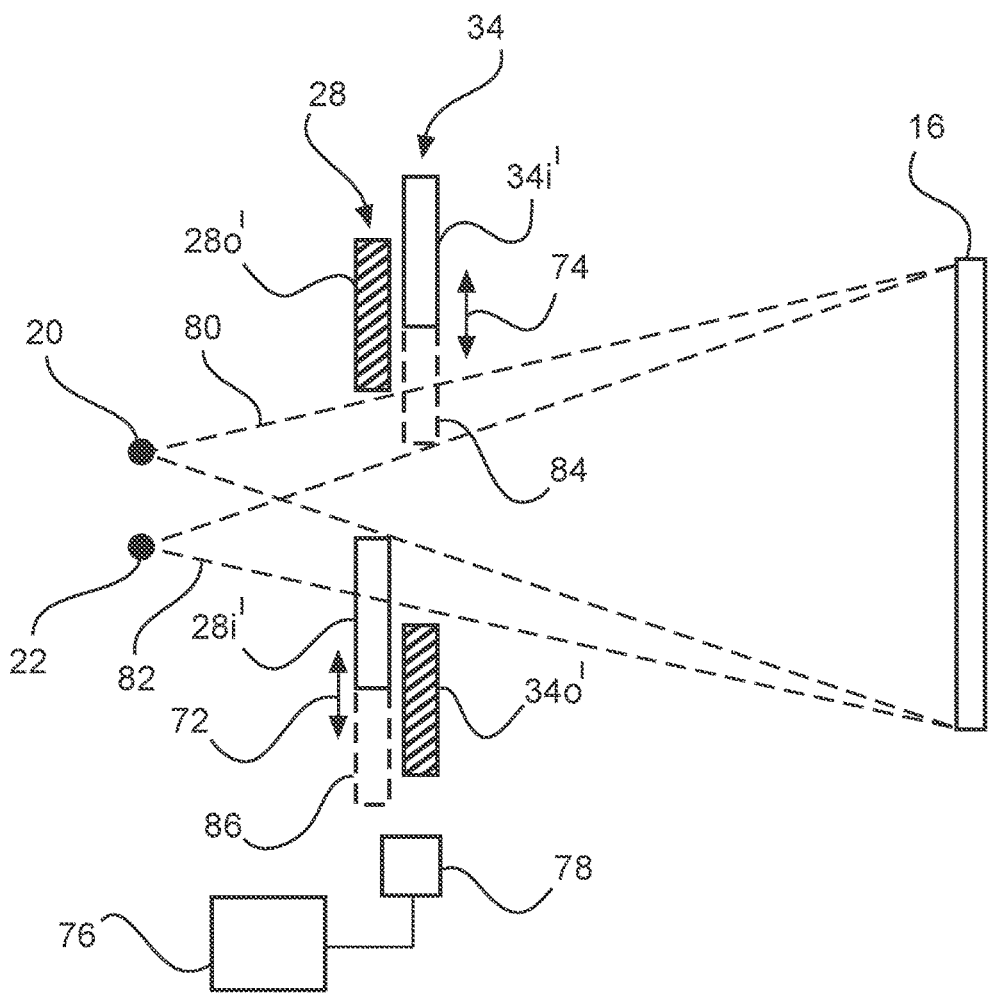
FIG. 5 shows an X-ray source arrangement in an example with movable shutter elements.

FIG. 5 shows a further example of the X-ray source arrangement 10, for example for slow moving focal spots or also for static focal spot positions. The first and the second pair of shutters, indicated with reference characters 28' and 34', comprise a respective first outer shutter element and a second outer shutter element. The first outer shutter element is indicated with reference character $28_O'$, and the second outer shutter element with $34_O'$. The respective first and second outer shutter elements are provided for limiting the diaphragm on an outer side arranged opposite an overlapping portion of the diaphragm. The first and the second pair of shutter elements 28', 34' further comprise a respective first and second inner shutter element, indicated with reference character $28_I'$ and $34_I'$.

The first and second inner shutter elements $28_I'$, $34_I'$ are provided for limiting the diaphragm on an inner side arranged at least partly in the overlapping portion.

It must be noted that in FIG. 5, the first pair of shutters 28' is provided in a first plane, and the second pair of shutters 34' is provided in a second plane. However, in a further example, the outer shutter elements, i.e. the first outer shutter element $28_O'$ and the second outer shutter element $34_O'$ are provided in a common outer shutter element plane. The inner shutter elements, i.e. the first inner shutter element $28_I'$ and the second inner shutter element $34_I'$, are provided in a common inner shutter elements plane (not further shown in detail).

In FIG. 4, the inner shutter elements are provided in a first curved plane, and the outer shutter elements are provided in a second curved plane. However, in a further example, the first shutter elements are provided in a first common curved plane, and the second shutter elements are provided in a second common plane (not further shown).

According to an example, the outer shutter elements are adjustably fixed for X-ray imaging. It is noted that this is not further indicated in FIG. 5.

According to a further example, as indicated in FIG. 5, the inner shutter elements $28_I'$, $34_I'$ are movable and configured for temporal alignment with the first line-of-sight between the first focal spot position 20 and the center of the detector 16, and for temporal alignment with the second line-of-sight between the second focal spot position 22 and the center of the detector 16.

The movability and adjustability of the first inner shutter element $28_I'$ is indicated with a first double arrow 72, and the movability/adjustability of the second inner shutter element $34_I'$ is indicated with a second double arrow 74.

The first and second focal spot positions 20, 22 are usable for X-ray radiation in an alternate manner during X-ray imaging. The first and the second inner shutter elements $28_I'$, $34_I'$ are alternately alignable during the X-ray imaging. The respective other second or first inner shutter element $34_I'$, $28_I'$ is movable out of the X-ray radiation. Further, a control unit 76 may be provided to control the alignment of the first and second inner shutter elements $28_I'$, $34_I'$ by an actuator arrangement 78 (not further shown in detail).

For example, FIG. 5 shows a situation where X-ray radiation is generated from the first focal spot position, providing a first X-ray beam 80. In this situation, the second inner shutter element $34_I'$ is moved out of the X-ray beam 80. For generating a second X-ray beam 82 for the second focal spot position 22, as indicated with dotted lines, the second inner shutter element $34_I'$ is moved to a second position, as indicated with dotted line structure 84, and the first inner shutter element $28_I'$ is also moved, namely out of the second X-ray beam 82, as indicated with position indicator 86 in dotted lines.

According to an example, the first and second focal spot positions 20, 22 are provided as movable positions (not further shown in FIG. 5) during X-ray image acquisition. The first and second inner shutter elements $28_I'$, $34_I'$ are aligned during the X-ray imaging.

According to a further example, the first and second inner shutter elements $28_I'$, $34_I'$ are aligned in a combined manner.

Figure 6:
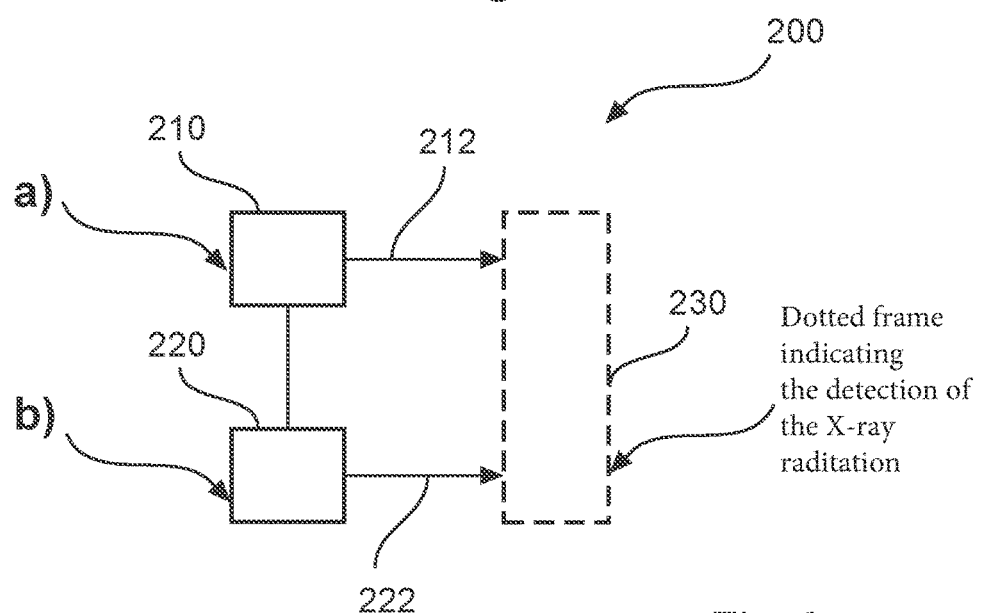
FIG. 6 shows an example of a method for X-ray image acquisition.

FIG. 6 shows basic steps of a method 200 for X-ray image acquisition, comprising the following steps:

In a first step 210, X-ray radiation is generated at a first focal spot position.

In a second step 220, X-ray radiation is generated at a second focal spot position distanced apart from the first focal spot position in a direction transverse to a main radiation direction. The first step 210 is also referred to as step a), and the second step 220 as step b). The generated X-ray radiation may be used for imaging an object, for example a patient, as indicated with a first arrow 212 for the first focal spot position in a first step 210, and with a second arrow 222 for the second focal spot position in a second step 220. A first pair of shutters is defining a first diaphragm for a first X-ray beam generated at the first focal spot position, and at least a second pair of shutters is defining a second diaphragm for a second X-ray beam generated at the second focal spot position. The first diaphragm is provided in step a), and the second diaphragm is provided in step b). The first pair of shutters is aligned with a first line-of-sight between the first focal spot position and the center of a detector, and the pair of shutters is aligned with a second line-of-sight between a second focal spot position and a center of the detector. The first and the second diaphragm partly overlap.

A dotted frame 230 indicates the detection of the X-ray radiation. Further image data processing may be provided, but is not indicated in more detail.

In an example, not further shown, a method is provided, where the first and second focal spot positions are provided as two static positions alternatively switched per frame for X-ray imaging. The first and second inner shutter elements remain fixed during the X-ray imaging. The first and the second pair of shutters each comprise an outer shutter element for limiting the diaphragm on an outer side arranged opposite an overlapping portion of the diaphragm, wherein the outer shutter elements comprise a solid structure in X-ray radiation direction. The first and the second pair of shutters comprise a respective first and second inner shutter element for limiting the diaphragm on an inner side arranged at least partly in the overlapping portion, wherein the first inner shutter element and the second inner shutter element each comprise a focal grid structure. Further, the grid structure of the first inner shutter element comprises a plurality of X-ray passages that are focused on the second focal spot position. The grid structure of the second inner shutter element comprises a plurality of X-ray passages that are focused on the first focal spot position.

In a further example, the first and second focal spot positions are provided as movable positions alternately switched per frame for X-ray imaging.

For example, the first and second inner shutter elements remain fixed in a temporal manner, i.e. they remain fixed in a particular imaging, but can be moved or adjusted before or after imaging.

In an example, a linear motor can be used to move shutters to the correct positions. For example, also piezo-elements can be provided for fine adjustment or fine movement.

It must be noted that the movement is provided in an example in one direction. In another example, two or more directions for correcting movement can be provided.

According to the invention, an example is provided where shutters, or also wedges, remain relatively fixed in images with moving focal spots.

In an example, a method is provided, where the first and second focal spot positions are provided as movable alternate focal spot positions during X-ray image acquisition. Outer shutter elements of the first and the second pair of shutters are limiting the diaphragm on an outer side arranged opposite an overlapping portion of the diaphragm. Inner shutter elements of the first and the second pair of shutters are limiting the diaphragm on an inner side, wherein the inner shutter elements are arranged at least partly in the overlapping portion. The outer shutter elements are remaining fixed for X-ray imaging, and the inner shutter elements are being moved for alternate temporal alignment with the first line-of-sight between the first focal spot position and the center of a detector, and aligning with a line-of-sight between the second focal spot position and a center of the detector.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray source arrangement for medical imaging, comprising:
   an X-ray source; and
   an X-ray beam shutter device;
   wherein the X-ray source is configured to generate X-ray radiation at least at a first and a second focal spot position distanced apart from each other in a direction (D) transverse to a main radiation direction (R);
   wherein the X-ray beam shutter device comprises at least a first pair of shutters defining a first diaphragm for a first X-ray beam generated at the first focal spot position, and at least a second pair of shutters defining a second diaphragm for a second X-ray beam generated at the second focal spot position, the first and the second diaphragm partly overlapping,
   wherein the first and the second pair of shutters each comprise an outer shutter element for limiting the diaphragm on an outer side arranged opposite an overlapping portion of the outer shutter elements comprising a solid structure in said radiation direction, and
   wherein the first and the second pair of shutters comprise a respective first and second inner shutter element for limiting the diaphragm on an inner side arranged at least partly in the overlapping portion,
   the inner shutter elements each comprising a focused grid structure, the grid structure of the first inner shutter element comprising a plurality of first X-ray passages being focused on the second focal spot position and the grid structure of the second inner shutter element comprising a plurality of second X-ray passages being focused on the first focal spot position.

2. X-ray source arrangement according to claim 1, wherein the first inner shutter element is arranged at least partly in an X-ray beam of the second focal spot position, the shutter element being X-ray transmissive for radiation from the second focal spot position; and wherein the second inner shutter element is arranged at least partly in an X-ray beam of the first focal spot position, the shutter element being X-ray transmissive for radiation from the first focal spot position.

3. X-ray source arrangement according to claim 1, wherein the first inner shutter element is movable on a first circular track around the second focal spot position; and the second inner shutter element is movable on a second circular track around the first focal spot position.

4. X-ray source arrangement according to claim 1, wherein the inner and outer shutter elements are provided with ring-segment cross sections with a center at one of the focal spot positions; and wherein:
   i) the first outer shutter element and the second inner shutter element are provided concentric to the first focal spot position; and
   ii) the first inner shutter element and the second outer shutter element are provided concentric to the second focal spot position.

5. X-ray source arrangement according to claim 1, wherein the first and second focal spot positions are provided as two static positions alternatively switched per frame for X-ray imaging; and wherein the first and second inner shutter elements remain temporarily fixed during the X-ray imaging.

6. X-ray source arrangement according to claim 1, wherein the first and second focal spot positions are provided as movable positions; and wherein the first and second inner shutter elements are adjustable to compensate for altering of the focal spot positions.

7. A medical X-ray imaging system, comprising:
an X-ray source arrangement according to claim 1;
an X-ray detector; and
an object-receiving device;
wherein the object-receiving device is positionable between the X-ray source arrangement and the X-ray detector.

8. Medical X-ray imaging system according to claim 7, wherein the first pair of shutters of the source arrangement is configured for being aligned with a first line-of-sight between the first focal spot position and a center of the detector, and the second pair of shutters of the source arrangement is configured for being aligned with a second line-of-sight between the second focal spot position and a center of the detector.

9. Medical X-ray imaging system according to claim 8, wherein the first and second inner shutter elements are configured for being aligned in a combined manner.

* * * * *